United States Patent
Sato et al.

(10) Patent No.: US 9,707,164 B2
(45) Date of Patent: Jul. 18, 2017

(54) POWDERED HAIR DYE COMPOSITION

(71) Applicant: HOYU CO., LTD., Nagoya-shi (JP)

(72) Inventors: Fumiaki Sato, Aichi-ken (JP); Emi Mori, Aichi-ken (JP); Yoshiyuki Uesawa, Aichi-ken (JP)

(73) Assignee: HOYU CO., LTD., Nagoya (JP)

(*) Notice: Subject to any disclaimer, the term of this patent is extended or adjusted under 35 U.S.C. 154(b) by 0 days.

(21) Appl. No.: 15/027,279

(22) PCT Filed: Oct. 7, 2013

(86) PCT No.: PCT/JP2013/077269
§ 371 (c)(1),
(2) Date: Apr. 5, 2016

(87) PCT Pub. No.: WO2015/052758
PCT Pub. Date: Apr. 16, 2015

(65) Prior Publication Data
US 2016/0243013 A1    Aug. 25, 2016

(51) Int. Cl.
| | |
|---|---|
| *A61Q 5/10* | (2006.01) |
| *A61K 8/46* | (2006.01) |
| *A61K 8/22* | (2006.01) |
| *A61K 8/41* | (2006.01) |
| *A61K 8/02* | (2006.01) |

(52) U.S. Cl.
CPC .............. *A61K 8/463* (2013.01); *A61K 8/022* (2013.01); *A61K 8/22* (2013.01); *A61K 8/411* (2013.01); *A61K 8/415* (2013.01); *A61Q 5/10* (2013.01); *A61K 2800/4324* (2013.01)

(58) Field of Classification Search
CPC ............ A61Q 5/10; A61K 8/22; A61K 8/411; A61K 8/022; A61K 8/463; A61K 8/415; A61K 8/4324
See application file for complete search history.

(56) References Cited

U.S. PATENT DOCUMENTS

2011/0203604 A1* 8/2011 Hasegawa ................ A61Q 5/10
132/208

FOREIGN PATENT DOCUMENTS

| EP | 2361604 A1 | 8/2011 |
|---|---|---|
| JP | 0381215 A | 4/1991 |
| JP | 04364114 A | 12/1992 |
| JP | 09169623 A | 6/1997 |

OTHER PUBLICATIONS

International Search Report, PCT/JP2013/077269, Jan. 7, 2014, pp. 1.

* cited by examiner

*Primary Examiner* — Eisa Elhilo
(74) *Attorney, Agent, or Firm* — Cantor Colburn LLP

(57) ABSTRACT

Provided is a powder hair dye composition capable of, in a hair-dyeing treatment intended to give a sharp black hue, suppressing the development of redness without being affected by the leave-on time required for the hair-dyeing treatment, while ensuring a sufficient hair-dyeing power. The powder hair dye composition contains (A) sodium percarbonate whose content is 1.8 to 3.7 mass % at the time of use, (B) p-phenylenediamine sulfate, and (C) m-aminophenol sulfate.

1 Claim, No Drawings

POWDERED HAIR DYE COMPOSITION

BACKGROUND OF THE INVENTION

The present invention relates to a powder hair dye composition. More specifically, the invention relates to a powder hair dye composition incorporating sodium percarbonate as an oxidizing agent and also incorporating a specific key intermediate and a coupler as an oxidation dye.

Conventionally, as hair dyes such as oxidation hair dyes, powder hair dyes have been provided. Powder hair dyes are usually one-agent type, and, at the time of use, they are dissolved in water, a water-based dissolving liquid of certain composition, or the like to form a paste, then applied to the hair, and left on for 30 to 40 minutes to perform a hair-dyeing treatment. Therefore, powder hair dyes can be produced, packaged, distributed, and stored in powder form, which is lightweight and easy to handle. This is advantageous in terms of cost as compared with hair dyes in cream form or solution form. Also for powder hair dye users, there are advantages in that, for example, the hair dye can be used in portions, is convenient to carry because of its light weight, and is easy to use.

A powder hair dye contains an oxidation dye and oxidizing agent in powder form, and usually also contains an alkaline agent in powder form. An oxidation dye may be composed only of a key intermediate, but is often composed of a key intermediate and a coupler. When an oxidation hair dye dissolved in water is allowed to act on the hair, melanin in the hair is decomposed by the action of the oxidizing agent, and also the oxidation dye is polymerized in the hair to form an oxidized dye polymer, whereby the hair is dyed to the desired hue. Persulfates, percarbonates, and the like are known as oxidizing agents. However, because persulfates are highly oxidative and may decompose the oxidized dye polymer, percarbonates such as sodium percarbonate are used in many cases.

The following PTL 1 discloses a powder hair dye composition containing an oxidation dye sulfate and sodium percarbonate that has a high active oxygen amount and is relatively highly oxidative, as well as a storage container having a configuration suitable for the storage thereof. The following PTL 2 discloses a powder hair dye composition containing an oxidation dye, an oxidizing agent such as sodium percarbonate, and a powdered silicone compound.

CITATION LIST

Patent Literature

PTL 1: EP 2361604 A1
PTL 2: JP-A-3-081215

SUMMARY OF INVENTION

Incidentally, it is often desired to dye the hair to a sharp black hue using a powder hair dye incorporating sodium percarbonate. In such a case, p-phenylenediamine is preferably selected as a key intermediate of an oxidation dye. Also in the case where p-phenylenediamine and other key intermediates are used together, it is preferable that the amount of p-phenylenediamine incorporated is larger. As a coupler to be used in combination with a key intermediate, m-aminophenol is preferable. In addition, as such a key intermediate or coupler, it is preferable to use a sulfate having excellent stability to an oxidizing agent.

However, it has been found that when a hair-dyeing treatment is performed using a powder hair dye incorporating sodium percarbonate as an oxidizing agent and also incorporating the above key intermediate and coupler as an oxidation dye, the dyed hair tends to have a more reddish hue than the intended dark hue. As a result of research, it has been found that this is caused by a rise in pH at the time of using the hair dye (during the leave-on time for the hair-dyeing treatment after the powder hair dye is dissolved in water and applied to the hair). It is believed that such a rise in pH relates to the following phenomenon: at the time of use, sodium percarbonate in powder form that has been mixed with water is decomposed to produce oxygen $O_2$ and sodium carbonate, which is a weak alkali, as shown in the following formula 1.

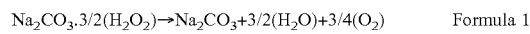

$$Na_2CO_3 \cdot 3/2(H_2O_2) \rightarrow Na_2CO_3 + 3/2(H_2O) + 3/4(O_2) \quad \text{Formula 1}$$

More specifically, in a powder hair dye incorporating sodium percarbonate and the above key intermediate and coupler, during the leave-on time of about 30 to 40 minutes for a hair-dyeing treatment (e.g., when the hair dye has been left on for about 20 minutes), the pH may rise to exceed a certain critical value (about pH 9). In the case where the pH exceeds the critical value, the hue of the dyed hair becomes reddish, making it impossible to dye the hair to a sharp black hue. In a hair dye incorporating a large amount of p-phenylenediamine for the purpose of giving a sharp black hue, this problem is particularly prominent.

When the hair-dyeing treatment is finished after a leave-on time of, for example, about 20 minutes to avoid this problem, the hair cannot be sufficiently dyed. Meanwhile, it has been found that when the amount of p-phenylenediamine incorporated is reduced, it becomes difficult to dye the hair to a sharp black hue, and, in addition, an increase in the relative amount of coupler (m-aminophenol) incorporated with respect to p-phenylenediamine also results in a reddish hue of the dyed hair.

Thus, an object to be achieved by the invention is to provide a powder hair dye composition capable of, in a hair-dyeing treatment intended to give a sharp black hue, suppressing the development of redness without being affected by the leave-on time required for the hair-dyeing treatment, while ensuring a sufficient hair-dyeing power.

Hereinafter, "at the time of use" regarding a powder hair dye means the state in which the powder hair dye is dissolved in water or a dissolving liquid, or the state in which the powder hair dye applied in such a state to the hair is subjected to a hair-dyeing treatment (during leave-on).

(First Invention)

The configuration of a first invention of this application is a powder hair dye composition comprising the following components (A) to (C):

(A) sodium percarbonate whose content is 1.8 to 3.7 mass % at the time of use;
(B) p-phenylenediamine sulfate;
(C) m-aminophenol sulfate.

(Second Invention)

The configuration of a second invention of this application is the powder hair dye composition according to the first invention, wherein the content of p-phenylenediamine sulfate (B) is at least 7.5 times the content of m-aminophenol sulfate (C) on mass basis.

Advantageous Effects of Invention

The problem that the dyed hair has a reddish hue due to a rise in pH at the time of using the hair dye is specifically attributable to a rise in pH exceeding a critical value (pH 9) during the leave-on time in the hair-dyeing treatment. Therefore, the key to solve the problem is to control the pH rise rate of the hair dye during the leave-on time. When the pH rise rate is slowed down so that it does not exceed pH 9 during the leave-on time of 30 minutes to 40 minutes required for hair dyeing, the hair can be sufficiently dyed to a sharp black hue.

Further, it is believed that a rise in the pH of a hair dye during the leave-on time in a hair-dyeing treatment is caused by sodium percarbonate, which is incorporated as an oxidizing agent. As a result of further experimental research on this point, it has been confirmed that when the amount of sodium percarbonate incorporated in a powder hair dye is such that the content thereof is 3.7 mass % or less at the time of use, the hair dye does not exceed pH 9 during the leave-on time of 30 minutes to 40 minutes required for hair dyeing, making it possible to sufficiently dye the hair to a sharp black hue. Meanwhile, in the case where the amount of sodium percarbonate incorporated in a powder hair dye is such that the content thereof is less than 1.8 mass % at the time of use, the amount of oxidizing agent is not enough, and thus an oxidized dye polymer is not sufficiently formed, making it impossible to sufficiently dye the hair.

The problem that the dyed hair has a reddish hue due to a rise in pH at the time of using the hair dye can be solved as described above. However, when the amount of p-phenylenediamine sulfate incorporated is reduced concerning the fact that this problem is prominent in the case where the amount of p-phenylenediamine sulfate incorporated is large as described above, then, because of the relative increase in the amount of m-aminophenol sulfate, which is a coupler, incorporated, the dyed hair has a reddish hue.

This problem can be avoided when the content of p-phenylenediamine sulfate (B) in the powder hair dye composition is at least 7.5 times the content of m-aminophenol sulfate (C) on mass basis. Incidentally, even when the content of component (B) in the powder hair dye composition is increased, as long as the composition has the configuration of the first invention or second invention, the problem that the dyed hair has a reddish hue due to a rise in pH at the time of using the hair dye does not occur.

DETAILED DESCRIPTION OF THE PREFERRED EMBODIMENTS

Next, modes for carrying out the invention will be described, including the best mode. The technical scope of the invention is not limited by the following embodiments.
[Powder Hair Dye Composition]

The powder hair dye composition of the invention is a composition in powder form for subjecting the hair to a hair-dyeing treatment, and examples thereof include oxidation hair dye compositions in powder form. The powder hair dye composition contains: as an oxidizing agent, sodium percarbonate (component (A)) incorporated in such an amount that the content thereof is 1.8 to 3.7 mass % at the time of use; p-phenylenediamine sulfate (component (B)) as a key intermediate of an oxidation dye; and m-aminophenol sulfate (component (C)) as a coupler of an oxidation dye. Usually, an alkaline agent is also contained, and a direct dye is also occasionally incorporated.

When the powder hair dye composition of the invention is used, similarly to ordinary powder hair dyes, the powder hair dye composition is dissolved in a suitable dissolving liquid such as water to prepare a chemical liquid in paste form, then applied to the hair using a comb, a brush, or the like, and left on for 30 minutes to 40 minutes, thereby dyeing the hair.

A certain mixing ratio between powder hair dye and dissolving liquid at the time of using the powder hair dye is previously set, and the amount of each component to be incorporated in the powder hair dye composition is determined considering such a mixing ratio. For example, the amount of component (A) incorporated described above also has to be determined by calculation considering this mixing ratio. The mixing ratio between powder hair dye and dissolving liquid in the powder hair dye composition of the invention can be set, for example, as a mass ratio within a range of about 1:1 to 1:20, more preferably about 1:2 to 1:10.
[Initial 1% pH]

As described above, sodium percarbonate in powder form mixed with water produces sodium carbonate, which is a weak alkali. In this relation, it has been found that under the condition where "alkaline agents other than sodium percarbonate are not contained", "initial 1% pH at the time of using the hair dye" can be effectively used as a novel, practical, simple index to predict/determine whether the hair dye of the invention will exceed pH 9 during a leave-on time of 30 minutes to 40 minutes. "Initial 1% pH" refers to the pH of a diluent prepared by dissolving the powder hair dye composition in a dissolving liquid such as water in a ratio to be employed at the time of use, immediately followed by 100-fold dilution with water.

Therefore, in the case where a powder hair dye composition that is designed to dye the hair to a sharp black hue and meets the above conditions is prepared, without actually using it on the hair for trial, or performing a hair-dyeing test using a hair tuft sample, when the initial 1% pH at the time of using the hair dye is 8.0 or less, particularly preferably 7.5 or less, it can be preparatorily confirmed that the hair dye is a hair dye that does not exceed pH 9 during a leave-on time of 30 minutes to 40 minutes at the time of use and does not give a reddish hue to the dyed hair.
[Main Components in Powder Hair Dye Composition]
(Component (A))

Component (A) is sodium percarbonate. From the reasons described in "Advantageous Effects of Invention" above, the amount of component (A) incorporated in the powder hair dye composition is (considering the mixing ratio between powder hair dye and dissolving liquid) such that the content thereof is 1.8 to 3.7 mass % at the time of use, more preferably such that the content thereof is 1.8 to 3.2 mass % at the time of use.
(Component (B) and Component (C))

Component (B) is p-phenylenediamine sulfate which is a key intermediate of an oxidation dye, while component (C) is m-aminophenol sulfate which is a coupler of an oxidation dye. The amounts of component (B) and component (C) incorporated in the powder hair dye composition are not limited, but it is preferable that the amount of component (B) is at least 7.5 times, more preferably at least 10 times, the amount of component (C) on mass basis. In addition, the amount of p-phenylenediamine sulfate incorporated in the powder hair dye composition is preferably such that the content thereof is 0.4 to 3.7 mass %, more preferably 0.9 to 2.8 mass %, at the time of use, and the amount of m-aminophenol sulfate incorporated in the powder hair dye composition is preferably such that the content thereof is 0.009 to 1.0 mass %, more preferably 0.09 to 0.5 mass %, at the time of use.

(Alkaline Agent)

In the powder hair dye composition of the invention, an alkaline agent is usually incorporated for the purpose of improving the dyeability. The powder hair dye composition of the invention contains sodium percarbonate as an essential component. When mixed with a liquid media such as water, powder sodium percarbonate is decomposed to produce sodium carbonate, which is an alkaline agent.

The powder hair dye composition of the invention may further contain optional powder alkaline agents. Examples of optional alkaline agents include sodium carbonate, magnesium carbonate, sodium metasilicate, basic amino acid, ammonium hydrogencarbonate, sodium hydrogencarbonate, potassium hydrogencarbonate, ammonium carbamate, potassium carbonate, guanidine carbonate, lithium carbonate, calcium carbonate, and ammonium sulfate.

Incidentally, it is also preferable that the powder hair dye composition of the invention does not contain optional powder alkaline agents.

The alkaline agent content in the powder hair dye is not particularly limited, but may be about 0 to 20 mass %, for example.

[Optional Components in Powder Hair Dye Composition]

In the powder hair dye composition of the invention, in addition to the above components, for example, oxidation dyes other than the component (B) and component (C), direct dyes, oil components, surfactants, pH adjusters, thickeners, chelating agents, dispersants, sodium sulfate, polypeptides, and the like may be suitably selected and incorporated in suitable amounts. Some of these components will be described hereinafter.

(Oxidation Dye Other than Component (B) and Component (C))

The powder hair dye composition of the invention may contain oxidation dyes other than the component (B) and component (C). Such oxidation dyes are selected from key intermediates and couplers.

Examples of key intermediates include toluene-2,5-diamine sulfate, paraaminophenol sulfate, orthoaminophenol sulfate, 2,2'-[4(-aminophenyl)imino]bisethanol sulfate, 1-hydroxyethyl-4,5-diaminopyrazole sulfate, and hydroxyethyl paraphenylenediamine sulfate.

Examples of couplers include 5-aminoorthocresol sulfate, 2,6-diaminopyridine sulfate, 2,4 diaminophenoxyethanol sulfate, paramethylaminophenol sulfate, 5-(2-hydroxyethylamino)-2-methylphenol sulfate, and metaphenylenediamine sulfate.

(Direct Dye)

Examples of direct dyes include acidic dyes, basic dyes, natural dyes, nitro dyes, and disperse dyes. These direct dyes may be incorporated alone or may also be incorporated in combination.

Examples of acidic dyes include Red No. 2, Red No. 3, Red No. 102, Red No. 104 (1), Red No. 105 (1), Red No. 106, Red No. 227, Red No. 230 (1), Yellow No. 4, Yellow No. 5, Yellow No. 202 (1), Yellow No. 202 (2), Yellow No. 203, Orange No. 205, Orange No. 207, Orange No. 402, Green No. 3, Green No. 204, Green No. 401, Purple No. 401, Blue No. 1, Blue No. 2, Blue No. 202, Brown No. 201, and Black No. 401.

Examples of basic dyes include Basic Blue 3, Basic Blue 6, Basic Blue 7, Basic Blue 9, Basic Blue 26, Basic Blue 41, Basic Blue 47, Basic Blue 99, Basic Brown 4, Basic Brown 16, Basic Brown 17, Basic Green 1, Basic Green 4, Basic Orange 1, Basic Orange 2, Basic Orange 31, Basic Red 1, Basic Red 2, Basic Red 22, Basic Red 46, Basic Red 51, Basic Red 76, Basic Red 118, Basic Violet 1, Basic Violet 3, Basic Violet 4, Basic Violet 10, Basic Violet 11:1, Basic Violet 14, Basic Violet 16, Basic Yellow 11, Basic Yellow 28, Basic Yellow 57, and Basic Yellow 87.

Examples of natural dyes include gardenia pigments, turmeric pigments, annatto pigments, sodium copper chlorophyllin, paprika pigments, and lac pigments.

Examples of nitro dyes include 4-nitro-o-phenylenediamine, 2-nitro-p-phenylenediamine, 2-amino-4-nitrophenol, 2-amino-5-nitrophenol, picramic acid, picric acid, salts thereof, HC Blue No. 2, HC Blue No. 5, HC Blue No. 6, HC Blue No. 9, HC Blue No. 10, HC Blue No. 11, HC Blue No. 12, HC Blue No. 13, HC Orange No. 1, HC Orange No. 2, HC Orange No. 3, HC Red No. 1, HC Red No. 3, HC Red No. 7, HC Red No. 10, HC Red No. 11, HC Red No. 13, HC Red No. 14, HC Violet No. 1, HC Violet No. 2, HC Yellow No. 2, HC Yellow No. 4, HC Yellow No. 5, HC Yellow No. 6, HC Yellow No. 9, HC Yellow No. 10, HC Yellow No. 11, HC Yellow No. 12, HC Yellow No. 13, HC Yellow No. 14, and HC Yellow No. 15.

Examples of disperse dyes include Disperse Black 9, Disperse Blue 1, Disperse Blue 3, Disperse Blue 7, Disperse Brown 4, Disperse Orange 3, Disperse Red 11, Disperse Red 15, Disperse Red 17, Disperse Violet 1, Disperse Violet 4, and Disperse Violet 15.

(Oil Component)

Examples of oil components include polyalcohols, oils and fats, waxes, higher alcohols, higher fatty acids, alkyl glyceryl ethers, esters, silicones, and hydrocarbons.

Examples of polyalcohols include glycols and glycerols. Examples of glycols include ethylene glycol, diethylene glycol, triethylene glycol, propylene glycol, dipropylene glycol, isoprene glycol, and 1,3-butylene glycol, while examples of glycerols include glycerol, diglycerol, and polyglycerol.

Examples of oils and fats include olive oil, rose hip oil, camellia oil, shea butter, macadamia nut oil, almond oil, teaseed oil, safflower oil, sunflower oil, soybean oil, cottonseed oil, sesame oil, tallow, cacao butter, corn oil, peanut oil, rapeseed oil, rice bran oil, rice germ oil, wheat germ oil, coix lacryma-jobi seed oil, grapeseed oil, avocado oil, carrot oil, castor oil, linseed oil, coconut oil, mink oil, and egg yolk oil.

Examples of waxes include beeswax (yellow wax), candelilla wax, carnauba wax, jojoba oil, lanolin, spermaceti wax, rice bran wax, cane wax, perm wax, montan wax, cotton wax, bayberry wax, and shellac wax.

Examples of higher alcohols include lauryl alcohol, myristyl alcohol, cetyl alcohol (cetanol), stearyl alcohol, cetostearyl alcohol, arachyl alcohol, behenyl alcohol, 2-hexyldecanol, isostearyl alcohol, 2-octyldodecanol, decyltetradecanol, oleyl alcohol, linoleyl alcohol, and lanolin alcohol.

Examples of higher fatty acids include lauric acid, myristic acid, palmitic acid, stearic acid, behenic acid, isostearic acid, hydroxystearic acid, 12-hydroxystearic acid, oleic acid, undecylenic acid, linoleic acid, ricinoleic acid, and lanolin fatty acid.

Examples of alkyl glyceryl ethers include batyl alcohol (monostearyl glyceryl ether), chimyl alcohol (monocetyl glyceryl ether), selachyl alcohol (monooleyl glyceryl ether), and isostearyl glyceryl ether.

Examples of esters include diisobutyl adipate, cetyl octanoate, isononyl isononanoate, diisopropyl sebacate, octyldodecyl myristate, isopropyl palmitate, stearyl stearate, hexyl laurate, hexyldecyl dimethyloctanoate, triisodecyl myristate, fatty acids ($C_{10-30}$) (cholesteryl/lanosteryl), lauryl lactate, lanolin acetate, ethylene glycol di-2-ethyl hexanoate, dipentaerythritol fatty acid ester, N-alkyl glycol monoisostearates, and diisostearyl malate.

Examples of silicones include dimethylpolysiloxane (INCI name: dimeticon), hydroxy-terminated dimethylpolysiloxane (INCI name: dimeticonol), methylphenyl polysiloxane, decamethyl cyclopentasiloxane, polyether-modified silicones, highly polymerized silicones having an average polymerization degree of 650 to 10000, amino-modified silicones, betaine-modified silicones, alkyl-modified silicones, alkoxy-modified silicones, and carboxy-modified silicones.

Among them, examples of amino-modified silicones include aminopropylmethylsiloxane-dimethylsiloxane copolymer (INCI name: aminopropyl dimeticon), aminoethylaminopropylsiloxane-dimethylsiloxane copolymer (INCI name: amodimethicone), and aminoethylaminopropylmethylsiloxane-dimethylsiloxane copolymer (INCI name: trimethylsilyl amodimethicone).

Examples of hydrocarbons include α-olefin oligomer, light isoparaffin, light liquid isoparaffin, liquid isoparaffin, liquid paraffin, squalane, polybutene, paraffin, microcrystalline wax, and Vaseline.

(Surfactant)

Examples of surfactants include cationic surfactants, anionic surfactants, amphoteric surfactants, and nonionic surfactants.

Examples of cationic surfactants include lauryltrimethylammonium chloride, cetyltrimethylammonium chloride, stearyltrimethylammonium chloride (steartrimonium chloride), distearyldimethylammonium chloride, behenyltrimethylammonium chloride (behentrimonium chloride), cetyltrimethylammonium bromide, stearyltrimethylammonium bromide, lanolin fatty acid aminopropylethyldimethylammonium ethylsulfate, stearyltrimethylammonium saccharin, cetyltrimethylammonium saccharin, and behenyltrimethylammonium methylsulfate.

Examples of anionic surfactants include sodium lauryl sulfate, sodium myristyl sulfate, ammonium lauryl sulfate, triethanolamine lauryl sulfate, sodium cetyl sulfate, sodium polyoxyethylene (hereinafter referred to as "POE") lauryl ether sulfate, triethanolamine POE lauryl ether sulfate, ammonium POE lauryl ether sulfate, sodium POE stearyl ether sulfate, triethanolamine dodecylbenzenesulfonate, sodium tetradecenesulfonate, sodium lauryl phosphate, POE lauryl ether phosphate and salts thereof, N-lauroyl glutamates (sodium lauroyl glutamate, etc.), N-lauroyl methyl-β-alanine salts, N-acylglycine salts, N-acylglutamates, lauric acid and myristic acid, which are higher fatty acids, and salts of these higher fatty acids, and alkyl sulfosuccinates.

Examples of amphoteric surfactants include lauryl betaine, imidazoline, amidobetaine, carbobetaine, sulfobetaine, hydroxy sulfobetaine, amide sulfobetaine, sodium 2-undecyl-N-carboxymethyl-N-hydroxyethyl imidazolinium betaine, cocoamidopropyl betaine, lauryldimethylaminoacetate betaine, and stearyldimethylaminoacetate betaine.

Examples of nonionic surfactants include ether surfactants such as POE cetyl ether, POE stearyl ether, POE lauryl ether, POE octyldodecyl ether, POE isostearyl ether, POE nonylphenyl ether, and POE octylphenyl ether, as well as ester surfactants such as POE sorbitan monooleate, POE sorbitan monolaurate, POE glycerol monostearate, POE sorbitol monolaurate, POE sorbitol beeswax, polyethylene glycol monolaurate, lipophilic glycerol monooleate, self-emulsified glycerol monostearate, sorbitan trioleate, sorbitan monopalmitate, sucrose fatty acid ester, decaglyceryl monolaurate, decaglyceryl monostearate, and decaglyceryl monomyristate.

(pH Adjuster)

Examples of pH adjusters include ammonium sulfate, ammonium nitrate, ammonium carbonate, ammonium chloride, primary ammonium phosphate, secondary ammonium phosphate, citric acid, tartaric acid, lactic acid, and succinic acid.

(Dispersant)

Examples of dispersants include metal stearate, silicic acid, metal silicate, talc, sucrose fatty acid ester, crystalline cellulose, and low-substituted hydroxypropyl cellulose.

(Chelating Agent)

Examples of chelating agents include disodium edetate, trisodium edetate, tetrasodium edetate, trisodium ethylenediaminehydroxyethyltriacetate, diethylenetriaminepentaacetic acid, sodium citrate, sodium metaphosphate, and sodium polyphosphate.

EXAMPLES

Hereinafter, examples and comparative examples of the invention will be described. The technical scope of the invention is not limited to these examples and comparative examples.

[Preparation of Powder Hair Dye Composition]

Powder hair dye compositions of Example 1 to Example 8 and Comparative Example 1 to Comparative Example 3 shown in Table 1 and Table 2, respectively, at the end were prepared. The components of the powder hair dye composition of each case are all in powder form. In addition, 3 g of the powder hair dye composition of each case is to be dissolved in 30 ml of water before use. That is, in all the examples and comparative examples, the mixing ratio between powder hair dye and dissolving liquid (water) at the time of use is substantially 1:10.

In Table 1 and Table 2, of the components, those corresponding to the components (A) to (C) of the invention are indicated with symbols "A" to "C", respectively, in the left-hand margin of each table.

In each case shown in Table 1 and Table 2, the value showing the content of each component is mass % in the powder hair dye composition. Therefore, the content of each component at the time of use can be calculated including the above mixing ratio. The content of component (A) specified in the first invention, that is, "1.8 to 3.7 mass % at the time of use", is equivalent to 19.8 to 40.7 mass % in the powder hair dye composition.

Further, after the preparation of the powder hair dye composition of each case, the composition was partially dissolved in water in accordance with the above mixing ratio and then immediately diluted 100-fold with water, and the pH of the diluent was measured. The "initial 1% pH at the time of use" of the powder hair dye composition of each of the examples and comparative examples thus measured is shown in the corresponding column of each table. In addition, the mass ratio of the content of component (B) to the content of component (C) in the powder hair dye composition of each case is shown in the "B/C" column of each table.

[Evaluation of Powder Hair Dye Composition]

With respect to the powder hair dye composition of each of the examples and comparative examples, a 10-g sample immediately after preparation was mixed with 100 ml of water and dissolved, then uniformly applied to a test white hair tuft, and left on for 30 minutes to perform a hair-dyeing treatment. After the completion of the hair-dyeing treatment, ten panelists visually observed the hair tuft to evaluate the hair-dyeing power of each hair dye and the redness of the hue of the dyed hair.

(Evaluation of Hair-Dyeing Power of Hair Dye)

The hair-dyeing power was evaluated based on whether the hair-dyeing power was "good" or "not good." In the case where eight or more out of ten panelists chose "good", rank "5" was given. In the case where six or seven chose "good", rank "4" was given. In the case where four or five chose "good", rank "3" was given. In the case where two or three chose "good", rank "2" was given. In the case where one or zero chose "good", rank "1" was given. The evaluation results are shown in the "Hair-dyeing power" column of each table.

(Evaluation of Redness of Hue of Dyed Hair)

The redness of the hue of the dyed hair was evaluated based on whether the hair had "clear black hue without redness" (positive evaluation) or "black hue with perceptible redness" (negative evaluation). In the case where eight or more out of ten panelists chose the positive evaluation, rank "5" was given. In the case where six or seven chose the positive evaluation, rank "4" was given. In the case where four or five chose the positive evaluation, rank "3" was given. In the case where two or three chose the positive evaluation, rank "2" was given. In the case where one or zero chose the positive evaluation, rank "1" was given. The evaluation results are shown in the "Redness" column of each table.

TABLE 1

|   |   | Examples | | | | | | | |
|---|---|---|---|---|---|---|---|---|---|
|   |   | 1 | 2 | 3 | 4 | 5 | 6 | 7 | 8 |
| A | Sodium percarbonate | 20 | 25 | 30 | 35 | 40 | 30 | 30 | 30 |
|   | Sodium carboxymethylcellulose | 20 | 20 | 20 | 20 | 20 | 20 | 20 | 20 |
|   | Sodium sulfate | 28 | 23 | 18 | 13 | 8 | 19 | 18 | 16 |
| B | p-Phenylenediamine sulfate | 30 | 30 | 30 | 30 | 30 | 30 | 30 | 30 |
| C | m-Aminophenol sulfate | 2 | 2 | 2 | 2 | 2 | 1 | 2 | 4 |
|   | Total | 100 | 100 | 100 | 100 | 100 | 100 | 100 | 100 |
|   | Content of component A at the time of use | 1.82 | 2.27 | 2.73 | 3.18 | 3.64 | 2.73 | 2.73 | 2.73 |
|   | Initial 1% pH | 6.1 | 6.4 | 6.7 | 7.1 | 7.3 | 6.8 | 6.8 | 6.8 |
|   | B/C | 15 | 15 | 15 | 15 | 15 | 30 | 15 | 7.5 |
|   | Hair-dyeing power | 4 | 5 | 5 | 5 | 4 | 5 | 5 | 4 |
|   | Redness | 5 | 5 | 5 | 4 | 3 | 5 | 5 | 4 |

TABLE 2

|   |   | Comparative Examples | | |
|---|---|---|---|---|
|   |   | 1 | 2 | 3 |
| A | Sodium percarbonate | 10 | 15 | 45 |
|   | Sodium carboxymethylcellulose | 20 | 20 | 20 |
|   | Sodium sulfate | 38 | 33 | 3 |
| B | p-Phenylenediamine sulfate | 30 | 30 | 30 |
| C | m-Aminophenol sulfate | 2 | 2 | 2 |
|   | Total | 100 | 100 | 100 |
|   | Content of component A at the time of use | 0.91 | 1.36 | 4.09 |
|   | Initial 1% pH | 4.1 | 5.7 | 8.5 |
|   | B/C | 15 | 15 | 15 |
|   | Hair-dyeing power | 1 | 2 | 4 |
|   | Redness | 5 | 5 | 2 |

INDUSTRIAL APPLICABILITY

According to the invention, a powder hair dye composition capable of, in a hair-dyeing treatment intended to give a sharp black hue, suppressing the development of redness without being affected by the leave-on time required for the hair-dyeing treatment, while ensuring a sufficient hair-dyeing power, is provided.

What is claimed is:

1. A powder hair dye composition comprising the following components (A) to (C):
   (A) sodium percarbonate whose content is 25 to 30 mass %;
   (B) p-phenylenediamine sulfate; and
   (C) m-aminophenol sulfate whose content is 1 to 2 mass %,
   wherein the content of p-phenylenediamine sulfate (B) is at least 7.5 times the content of m-aminophenol sulfate (C) on mass basis, and in a case where an initial 1% pH refers to the pH of a diluent prepared by dissolving the powder hair dye composition in a dissolving liquid in a ratio to be employed at the time of use, immediately followed by 100-fold dilution with water, the initial 1% pH at the time of using the hair dye composition is 8.0 or less.

* * * * *